(12) United States Patent
Melnyk et al.

(10) Patent No.: US 10,072,041 B2
(45) Date of Patent: Sep. 11, 2018

(54) METHOD FOR PREPARING PEPTIDES BY ASSEMBLING MULTIPLE PEPTIDE FRAGMENTS

(75) Inventors: Oleg Melnyk, Annoeullin (FR); Nathalie Ollivier, Roubaix (FR); Reda Mhidia, Mons en Baroeul (FR); Julien Dheur, La Bassee (FR)

(73) Assignees: Centre National de la Recherche Scientifique, Paris (FR); Universite de Lille 1 Sciences et Technologies, Villeneuve D'Ascq (FR)

( * ) Notice: Subject to any disclaimer, the term of this patent is extended or adjusted under 35 U.S.C. 154(b) by 363 days.

(21) Appl. No.: 13/985,369

(22) PCT Filed: Feb. 15, 2012

(86) PCT No.: PCT/EP2012/052548
§ 371 (c)(1),
(2), (4) Date: Aug. 14, 2013

(87) PCT Pub. No.: WO2012/110536
PCT Pub. Date: Aug. 23, 2012

(65) Prior Publication Data
US 2013/0331545 A1 Dec. 12, 2013

(30) Foreign Application Priority Data
Feb. 16, 2011 (FR) ...................... 11 51279

(51) Int. Cl.
*C07K 1/26* (2006.01)
*C07K 1/02* (2006.01)
*C07K 1/00* (2006.01)

(52) U.S. Cl.
CPC .............. *C07K 1/026* (2013.01); *C07K 1/003* (2013.01)

(58) Field of Classification Search
None
See application file for complete search history.

(56) References Cited

U.S. PATENT DOCUMENTS

| | | | | |
|---|---|---|---|---|
| 9,029,503 B2 * | 5/2015 | Melnyk | .................. | C07K 1/026 530/330 |
| 9,206,224 B2 * | 12/2015 | Melnyk | .................. | C07K 1/026 |
| 9,796,758 B2 * | 10/2017 | Melnyk | .................. | C07K 1/088 |
| 2013/0331545 A1 * | 12/2013 | Melnyk et al. | ............... | 530/339 |

FOREIGN PATENT DOCUMENTS

| WO | WO-96/34878 A1 | 11/1996 |
|---|---|---|
| WO | WO-98/28434 A1 | 7/1998 |
| WO | WO-01/68565 AI | 9/2001 |
| WO | WO-01/87920 AI | 11/2001 |
| WO | WO-2007/037812 A1 | 4/2007 |

OTHER PUBLICATIONS

Camarero, J.A. et al.—UNIT18.4: Native Chemical Ligation of Polypeptides, Current Protocols in Protein Science (2001) pp. 18.4.1-18.4.21 (cited by IDS).*
Ollivier, N. et al., Bis(2-sulfanylethyl)amino Native Peptide Litigation, Organic Letters, vol. 12, No. 22 (2010) pp. 5238-5241 (cited by IDS).*
Ollivier et al. "Bis (2-sulfanylethyl)amino Native Peptide Ligation", Organic Letters, vol. 12, No. 22, Nov. 19, 2010, pp. 5238-5241.*
International Search Report for Application No. PCT/EP2012/052548, dated May 22, 2012.
Bang, D. et al., *Kinetically Controlled Ligationg for the Convergent Chemical Synthesis of Proteins*, Angew. Chem. Int. Ed., vol. 46 (2006) pp. 3985-3988.
Camarero, J.A. et al., *Native Chemical Ligation of Polypeptides*, Unit18.4; Current Protocols in Protein Science (1999) pp. 18.4.1-18.4.21
Hou, W. et al., *Peptidyl N,N-Bis(2-mercaptoethyl)-amides as Thioester Precursors for Native Chemical Litigation*, Organic Letters, vol. 13, No. 3 (2010) 386-389
Ollivier, N. et al., *Bis(2-sulfanylethyl)amino Native Peptide Litigation*, Organic Letters, vol. 12, No. 22 (2010) pp. 5238-5241
Written Opinion for International Application No. PCT/EP2012/052548 dated May 22, 2012.

* cited by examiner

*Primary Examiner* — Maury A Audet
(74) *Attorney, Agent, or Firm* — Alston & Bird LLP

(57) ABSTRACT

Method for preparing a peptide assembly of n fragments and n−1 amino acids bearing a thiol function, represented by the formula:

$$A_1\text{-}C_1\text{-}A_2\text{-}C_2\text{-}A_3\text{-} \ldots \text{-}C_{i-1}\text{-}A_i\text{-} \ldots \text{-}C_{n-1}\text{-}A_n \qquad (I)$$

in which $A_1, A_2, A_3, \ldots A_i \ldots, A_n$ are peptide fragments, $C_1, C_2, C_3 \ldots C_{i-1} \ldots C_{n-1}$ are amino acid residues bearing a thiol function, n is comprised between 3 and 50, and i is 2 to n, in which a peptide-thioester is prepared of formula: $A_1\text{-}SR$ (II) in which $A_1$ is a peptide fragment and SR is an alkyl thioester residue, R being alkyl optionally substituted, starting from a bis(2-sulphanylethyl)amino peptide.

10 Claims, No Drawings
Specification includes a Sequence Listing.

METHOD FOR PREPARING PEPTIDES BY ASSEMBLING MULTIPLE PEPTIDE FRAGMENTS

FIELD OF THE INVENTION

The present invention relates to a method for preparing peptides or polypeptides by assembling multiple peptide fragments, using native ligation of polypeptides. The invention also relates to the preparation of intermediates used in this method and said intermediates prepared by the method.

TECHNOLOGICAL BACKGROUND

The synthesis of polypeptides by conventional solid phase methods, amino acid by amino acid, is limited by low yields when the polypeptides synthesized are large in size. In order to overcome this limitation, it is known to assemble two polypeptides by chemical ligation in order to produce a longer polypeptide.

The total synthesis of polypeptides is increasingly useful for the preparation of proteins with well-defined structures. The chemical ligation methods provide a response to this need, however they prove limited in their use and their industrial application.

Generally, in these methods, it is desired that the bond between the polypeptides assembled by ligation is native, i.e. corresponds to the natural structure of the polypeptides.

The main native ligation method currently existing is that of Kent and Dawson, described for example in the international applications WO 96/34878 and WO 98/28434. This method is based on a chemoselective reaction between a (C-terminal) thioester peptide and a cysteinyl-peptide. Nevertheless, the main drawback of this method is the production of thioester peptides which requires complex chemical processes. In particular, according to an assembly method described by S. Kent (Kinetically Controlled Ligation (KCL)), it is necessary to synthesize the A-SAr, H-Cys-B-SAlk, and H-Cys-C fragments. However A-SAr type fragments are difficult to produce and prove to be susceptible to hydrolysis. Furthermore, this method does not make it possible to go beyond the assembly of 3 fragments.

An alternative method is the so-called Staudinger ligation, described in the international applications WO 01/68565 and WO 01/87920. This comprises the reaction of a phosphino-thioester with an azide and the hydrolysis of the combined reagents to form an amide bond. However this method is difficult to apply on an industrial scale.

Another method, described in the international application WO 2007/037812, is based on the reaction of an α-keto acid with an alkoxyamine in a decarboxylative condensation reaction. However, the keto acids are molecules which are difficult to produce and to incorporate into peptides. Also, this third method is difficult to apply in peptide synthesis laboratories that do not have the means for carrying out complex organic syntheses.

The publication by D. Bang, B. L. Pentelute and S. B. H. Kent, Angew. Chem. Int. Ed. 2006, 45, 3985-3988 proposes a synthesis route involving peptide-(thiophenylesters) with Cys-peptide-thioesters, and the publication by W. Hou et al., Org Lett., (2010), 22 Dec. 2010, proposes the formation of peptide-thioesters for the synthesis of proteins. However these methods cannot prevent competition between the reactions of the different thioesters, inevitably leading to mixtures that can be difficult to separate, therefore affecting the purity of the final product obtained, and to inevitable losses of yield.

Finally, the publication by O. Melnyk et al., Org. Lett., 12(22), 5238-41 (2010) describes the native ligation of peptides by means of peptide-bis(sulphanylethyl)amino fragments. However this method has never to date been used for the synthesis of peptides with multiple fragments.

The transfer to the industrial scale of methods making it possible to implement peptide syntheses by total synthesis is a need that requires methods to be found which are simple, inexpensive, producing quality products of high purity which satisfy industrial health requirements.

For the abovementioned reasons, it has become essential to find a total synthesis method, which is coherent and can be used on an industrial scale, making it possible to synthesize a peptide chain formation of the desired length and nature. Particularly a method involving assembly from the N-terminal end towards the C-terminal end, which offers qualities of simplicity of production and purity of the peptides or polypeptides obtained.

DESCRIPTION OF THE INVENTION

It has been found, which forms the subject of the present invention, that assembling multiple peptide fragments in a one-pot method involving simple methods such as the formation of peptide-thioesters and native ligation, could lead to a total synthesis method, which is convergent, can be used on an industrial scale and corresponds to the required purity criteria.

According to the invention, the assembly method involves the synthesis of peptide-thioesters, their condensation reaction with a peptide (or polypeptide) bearing a bis(2-sulphanylethyl)amino function in the cyclic disulphide state, corresponding to the general formula:

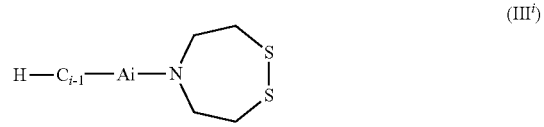

(III$^i$)

in which
$A_i$ represents a peptide fragment the C-terminal end of which bears a
cyclic bis(2-sulphanylethyl)amino

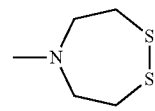

group hereafter called SEAoff
and $C_{i-1}$ represents an amino acid residue bearing a thiol function,
as well as native chemical ligation in a reducing medium, at the C-terminal end, of the polypeptides obtained.

It is understood that the term SEAoff means non-reactive cyclic disulphide, as opposed to the reactive disulphide of structure $-N[(CH_2)_2-SH]_2$ hereafter called SEAon.

It is understood that the amino acid bearing a thiol function represented by $C_{i-1}$ can be in particular chosen from cysteine, homocysteine, and that these amino acids bear a disulphide residue (SR') on the thiol of the amino acid, in the implementation of the reaction with the peptide-thioester.

According to the invention, the method leads to the preparation of a multiple peptide assembly comprising the amino acid residues bearing a thiol function, i.e. a peptide assembly of n fragments and of n−1 amino acids bearing a thiol function, represented by the formula:

$$A_1\text{-}C_1\text{-}A_2\text{-}C_2\text{-}A_3\text{-} \ldots \text{-}C_{i-1}\text{-}A_i\text{-} \ldots \text{-}C_{n-1}\text{-}A_n \quad (I)$$

in which $A_1, A_2, A_3, \ldots A_i, \ldots, A_n$ are peptide fragments, $C_1, C_2, C_3 \ldots C_{i-1} \ldots C_{n-1}$ are amino acid residues bearing a thiol function,
n is comprised between 3 and 50,
preferably between 3 and 20,
or even more preferably between 3 and 10, and
i is any integer comprised between 2 and n.
It is understood that, when n=3, $C_{n-1}\text{-}A_n$ represents $C_2\text{-}A_3$ and $C_{i-1}\text{-}A_i$ represents $C_1\text{-}A_2$.
In this case the peptide assembly of formula (I) is of structure: $A_1\text{-}C_1\text{-}A_2\text{-}C_2\text{-}A_3$.

The method according to the invention consists of the preparation of a peptide-thioester of formula:

$$A_1\text{-SR} \quad (II)$$

in which $A_1$ is a peptide fragment and SR is an alkylated thioester residue, R being able to be an optionally substituted alkyl radical,
from a bis(2-sulphanylethyl)amino peptide $A_1$-SEAoff in which SEAoff is defined as previously,
by the action of a thiol R—SH, in the presence of a cyclic disulphide reducing agent,
followed by condensation with a peptide fragment of structure:

$$H\text{—}C_1(SR')\text{-}A_2\text{-SEAoff} \quad (III)$$

in which $C_1$, $A_2$ and SEAoff are defined as above and (SR') represents a disulphide residue on the thiol of the amino acid $C_1$, in the presence of an aromatic thiol ArSH,
then conversion of the new peptide fragment obtained, of structure:

$$A_1\text{-}C_1\text{-}A_2\text{-SEAoff} \quad (IV)$$

in which $A_1, C_1, A_2$ and SEAoff are as defined previously, to a peptide-thioester of formula:

$$A_1\text{-}C_1\text{-}A_2\text{-SR} \quad (II')$$

in which $A_1, C_1, A_2$ and R are as defined previously, by the action of a thiol R—SH, in the presence of a cyclic disulphide reducing agent,
followed by condensation with a peptide fragment of structure:

$$H\text{—}C_2(SR')\text{-}A_3\text{-SEAoff} \quad (III')$$

in which SEAoff and R' and $C_2$ and $A_3$ are as defined above, in the presence of an aromatic thiol ArSH, in order to produce a peptide fragment, of structure:

$$A_1\text{-}C_1\text{-}A_2\text{-}C_2\text{-}A_3\text{-SEAoff} \quad (IV')$$

in which $A_1, C_1, A_2, C_2, A_3$ and SEAoff are as defined previously,
then reiteration of these 2 operations up to n−2 times, in order to obtain a peptide fragment of structure:

$$A_1\text{-}C_1\text{-}A_2\text{-}C_2\text{-}A_3\text{-} \ldots \text{-}C_{i-1}\text{-}A_i\text{-} \ldots \text{-}C_{n-2}\text{-}A_{n-1}\text{-SEAoff} \quad (IV''')$$

in which $A_1, A_2, A_3, \ldots A_i, \ldots, A_{n-1}, C_1, C_2, C_3 \ldots C_{i-1} \ldots C_{n-2}$ and SEAoff are as defined previously, and implementation of a native ligation reaction of this obtained peptide fragment (IV'''), with a peptide of formula:

$$H\text{—}C_{n-1}\text{-}A_n \quad (V''')$$

in which $C_{n-1}$ and $A_n$ are as defined previously, by reduction in the presence of a cyclic disulphide reducing agent, in order to produce the multiple peptide assembly of general formula (I).

DESCRIPTION OF EMBODIMENTS OF THE INVENTION

The invention is now described in more detail and non-limitatively in the description which follows.

By "peptides or polypeptides" is meant, in the context of the present application, a linear chain of amino acid residues (in a number greater than or equal to two) linked by peptide bonds. The "peptides or polypeptides" within the meaning of the present application can therefore for example be oligopeptides, peptides or proteins according to the conventionally accepted meaning of these words. The amino acid residues present in the polypeptides according to the invention can be chosen from the proteinogenic or non-proteinogenic amino acid residues. Preferably, they are chosen from the twenty proteinogenic or amino acid residues.

Polypeptide notation is from the N-terminal end to the C-terminal end. The amino acid residues present along the polypeptide chain are denoted according to the usual one-letter or three-letter code. An amino acid residue is a polypeptide fragment of formula —NH—(CH—R)—(C=O)—, in which R represents a side chain, which differs from one amino acid to another.

By "peptide fragment" is meant, in the context of the present application, a portion of polypeptide comprising at least one amino acid residue. A peptide fragment, within the meaning of the present application, can therefore be for example: a sequence of amino acid residues (such as -AHG- or -Ala-His-Gly-) if the peptide fragment comprises neither the N-terminal end nor the C-terminal end of the polypeptide; or a sequence of amino acid residues having a group at its N-terminal end (such as H-AHG- or H-Ala-His-Gly-) if the peptide fragment comprises the N-terminal end of the polypeptide; or a sequence of amino acid residues having a group at its C-terminal end (such as -AHG-OH or -Ala-His-Gly-OH) if the peptide fragment comprises the C-terminal end of the polypeptide.

It is understood that each of the peptide fragments preferably comprises only acid residues chosen from the 20 proteinogenic or amino acid residues. However, according to a particular embodiment, the peptide fragments $A_i$ in an internal position in the sequence can also comprise one or more non-proteinogenic amino acid residues, the one or more of the peptide fragments $A_2 \ldots A_i \ldots A_{n-1}$ being able to bear one or more modified amino acids, the modification being put into place prior to the implementation of the method. By way of non-limitative example, the modification of the amino acids can in particular be chosen from radicals chosen from carboxylic acid residues (biotin, acetyl group, aminooxyacetic residue, a fluorophore such as tetramethylrhodamine, a metal chelating agent such as 1,4,7,10-tetraazacyclododecane-1,4,7,10-tetraacetic acid (DOTA), a lipid such as palmitic acid, a polymer such as for example alpha-methoxy-omega-carboxy poly(ethylene glycol) or others. Or also from post-translational modifications of proteinogenic amino acids known to a person skilled in the art (methylation, phosphorylation, acetylation, glycosylation, sulphation, hydroxylation, carboxymethylation, bearing appropriate protections for solid phase incorporation, etc.), or optionally a medicament (the protein then serving as vector).

A modification can be introduced simply by using a non-proteinogenic amino acid, in particular a proteinogenic amino acid derivative, in order to introduce the modification during the solid phase synthesis of the fragment considered. By way of example, it is possible to use an Fmoc-L-Lys (Biotin)-OH, i.e. a lysine bearing a biotin on its side chain, in order to carry out the synthesis of a fragment. This fragment is then involved in the assembly in a manner identical to that which uses proteinogenic amino acid fragments.

According to an embodiment of the invention, a peptide fragment $A_i$ comprises between 2 and 300 amino acid residues, preferably between 5 and 100 amino acid residues, more particularly preferably between 8 and 50 amino acid residues.

The alkyl radical represented by R is an alkyl radical of 1 to 12 carbon atoms, linear or branched, optionally substituted by one or more groups chosen from the halogen atoms (F for example), or the $CO_2H$, $SO_3H$, $CONH_2$, OH, SH, alkyloxy, alkylthio, mercaptoalkylthio radicals, an ester residue or a polyethylene glycol residue, or by an optionally substituted phenyl, or other organic groups which do not interfere with the reactions implemented. The thiol of general formula R—SH can be for example $HSCH_2CH_2CO2H$, $HSCH_2CH_2SO3H$, $HSCH_2CH_2SH$, $HSCH_2CH_2SCH_2CH_2SH$ or $HSCH_2Ph$.

The aromatic thiol is advantageously chosen from disulphide bond reducing compounds, preferably chosen from thiophenol and/or the derivatives obtained by substitution of the aromatic ring, for example 4-carboxymethylthiophenol, 4-mercaptophenylacetic acid, dithiothreitol, benzylmercaptan and mixtures thereof.

The SEAoff reducing agent can be chosen from the cyclic disulphide reducing agents. It can be in particular chosen from the phosphines (for example tris (2-carboxyethyl) phosphine), or any other cyclic disulphide reducing agent such as the thiols (for example dithiothreitol (DTT)).

An example of Peptide $A_1$-SEAoff can be represented by the formula:

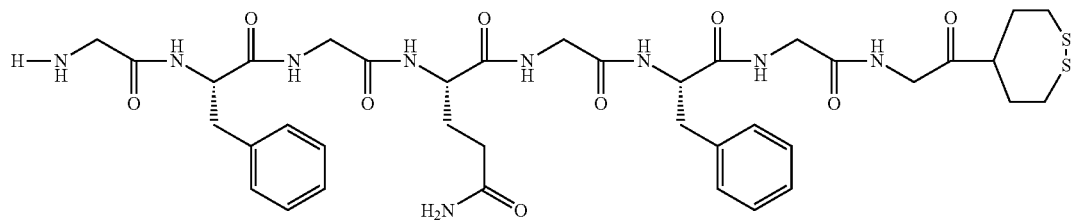 [SMILES: NCC(=O)N[C@@H](Cc1ccccc1)C(=O)NCC(=O)N[C@@H](CCC(N)=O)C(=O)NCC(=O)N[C@@H](Cc1ccccc1)C(=O)NCC(=O)NCC(=O)C1CCSSCC1]

in this example, the peptide fragment $A_1$ is H-GFGQGFGG (SEQ ID NO: 1).

It is understood that the peptide fragment $A_n$ may have been prepared beforehand by a sequence of operations as described above, according to the method of the invention.

According to the invention, the method for assembling multiple peptide fragments can be represented according to Diagram 1 below:

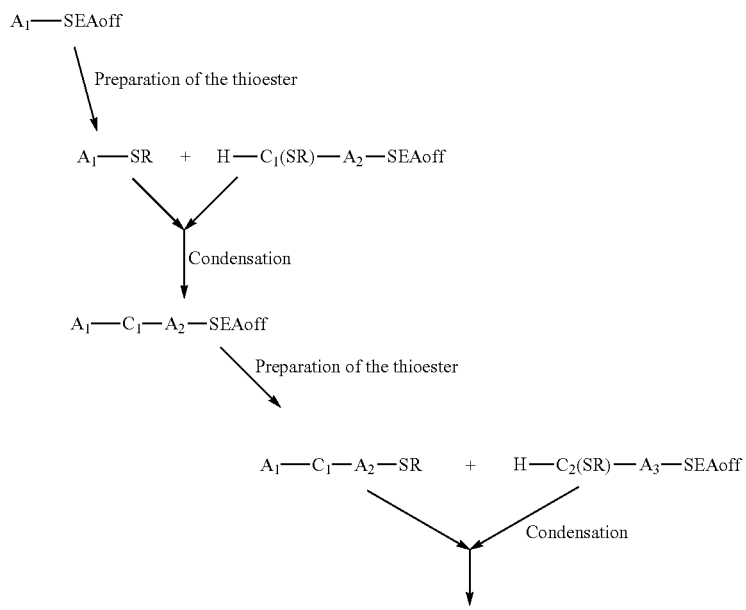

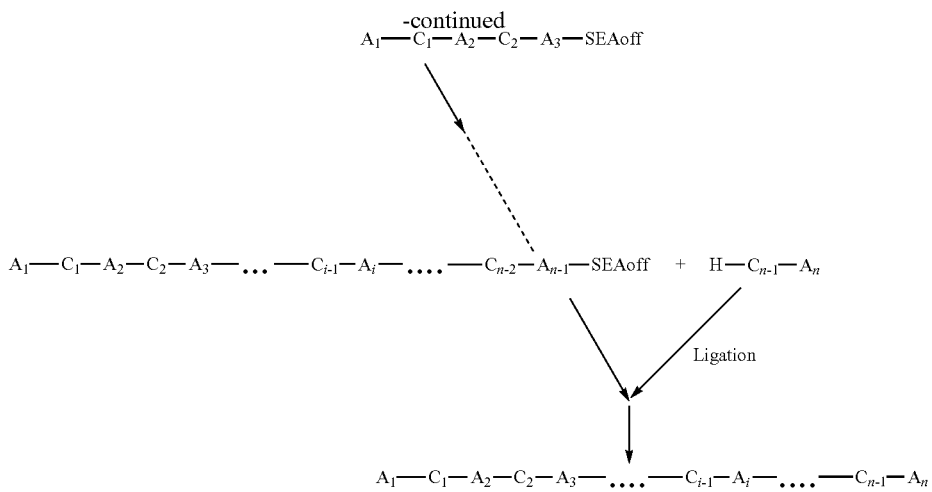

All of the multiple peptide assembly preparation reactions have the great advantage of being able to be implemented in situ, in a "one pot" reaction, particularly when the number of peptide fragments n is equal to 3, without it being necessary to isolate the intermediates formed.

The method according to the invention can be carried out as described below, and as illustrated in the following examples.

The preparation of the peptide-thioesters of formula (II) is advantageously implemented by the action of an alkylthiol the alkyl part of which is optionally substituted on a bis(2-sulphanylethyl)amino peptide: $A_1$-SEAoff, in the presence of a cyclic disulphide reducing agent such as in particular a phosphine, for example tris(2-carboxyethyl)phosphine. The reaction is advantageously carried out under an inert atmosphere (under argon for example), at a pH comprised between 1 and 8, preferably at pH 4 and at a temperature comprised between 20 and 50° C. Advantageously 3-mercaptopropionic acid is used.

The condensation of the thioester of formula (II) with the peptide fragment of general formula (III): $H-C_1(SR')-A_2$-SEAoff, is advantageously carried out in the presence of an aromatic thiol (in particular 4-mercaptophenylacetic acid), by operating under an inert atmosphere (under argon for example), at a temperature comprised between 20 and 60° C. It is not necessary to isolate the obtained peptide fragment in order to use it in the following reaction.

The native ligation reaction of the peptide fragment (IV''') ($A_1$-$C_1$-$A_2$-$C_2$-$A_3$- . . . -$C_{i-1}$-$A_i$- . . . -$C_{n-2}$-$A_{n-1}$-SEAoff) with the peptide (V'') (H—$C_{n-1}$-$A_n$) is implemented by the action of a cyclic disulphide reducing agent, which can preferably be a phosphine (for example tris(2-carboxyethyl)phosphine (TCEP)) a thiol compound such as 4-mercaptophenylacetic acid (MPAA), dithiothreitol (DTT), thiophenol (and its derivatives), an alkylthiol (in particular benzylmercaptan) or also mixtures of several of these compounds, for example MPAA and TCEP, by operating under an inert atmosphere (under argon for example), at a temperature comprised between 20 and 60° C., preferably at a temperature of 37° C. The reaction is carried out in particular in aqueous medium, for example in a phosphate buffer. It is preferably carried out at a pH comprised between 5.5 and 8.5, more particularly preferably at a pH comprised between 6 and 8 and ideally at a pH of approximately 7. The duration of the reaction depends on the reagents used, it is monitored and adjusted according to the results of liquid chromatography analysis. It is not necessary to isolate the obtained peptide fragment (IV''') in order to use it in the native ligation reaction. It is understood that the reaction of the cyclic disulphide reducing agent can be implemented on the peptide fragment of formula (IV''') before or simultaneously with the reaction with the peptide of formula (V'').

According to a particular embodiment, the peptide fragments of formula (IV''') and (V'') comprise one or more non-proteinogenic amino acid residues.

The amino acid residues of the polypeptides of formula (IV''') and (V'') can optionally be protected by side-chain protective groups. The protection and removal of the protective radicals can be carried out according to known methods which do not alter the remainder of the molecule. More particularly according to the methods described by T. Greene and P. Wuts, *Protective groups in organic synthesis,* 2nd edition, John Wiley & Sons, Inc.

The preparation of the bis(2-sulphanylethyl)amino peptide: $A_1$-SEAoff can be carried out according to the method described by Melnyk, O. et al., Bis(2-sulphanylethyl)amino native peptide ligation., Org. Lett., 12(22), 5238-41 (2010). According to the procedure of this method, the coupling of an amino acid to a polymer resin support comprises bringing the polymer resin support into contact with an amino acid halide or with an amino acid and an activation agent, preferably chosen from PyBOP® (benzotriazol-1-yl-oxytripyrrolidinophosphonium hexafluorophosphate), BOP, PyBroP® (bromo-tris-pyrrolidinophosphonium hexafluorophosphate), or also HATU (2-(1H-7-azabenzotriazol-1-yl)-1,1,3,3-tetramethyl uronium hexafluorophosphate methanaminium) and more particularly preferably PyBroP. This procedure is described in more detail below, in the examples of the preparation of the starting peptide fragments.

In particular, the corresponding peptides-$N(CH_2CH_2SH)_2$ (SEAon peptides) are oxidized by the air, under stirring, in a 0.1M ammonium bicarbonate solution, at ambient temperature. Advantageously, they can also be obtained by oxidation in the presence of iodine or diamide, $(CH_3)_2NCON=NCON(CH_3)_2$.

The polypeptide of formula (V'') can for example be obtained by a usual peptide synthesis method, in particular a solid phase synthesis method. It can also be obtained by means of native ligation as described in Org. Lett., 12(22), 5238-41(2010).

According to preferred embodiments of the present invention, a peptide assembly of 3 or 4 fragments is prepared, of structures $A_1$-$C_1$-$A_2$-$C_2$-$A_3$ or $A_1$-$C_1$-$A_2$-$C_2$-$A_3$-$C_3$-$A_4$.

According to another preferred embodiment of the invention, the $C_i$ amino acids bearing a thiol function are cysteine Cys residues.

In this case, according to a preferred embodiment of the invention, a peptide assembly of structure $A_1$-Cys-$A_2$-Cys-$A_3$ or $A_1$-Cys-$A_2$-Cys-$A_3$-Cys-$A_4$ is prepared.

According to these preferred embodiments, the peptide assembly preparation diagram can be represented according to Diagram 2 below:

the manufacture of a polypeptide or peptide according to the method for manufacturing a polypeptide of formula (I) described previously, and the pharmaceutical compositions comprising a polypeptide or peptide thus prepared, in the pure state or in combination with one or more compatible and pharmaceutically acceptable adjuvants.

The invention also relates to a method for manufacturing a diagnostic device comprising:

the manufacture of a polypeptide or peptide according to the method for manufacturing a polypeptide of formula (I) described previously, and

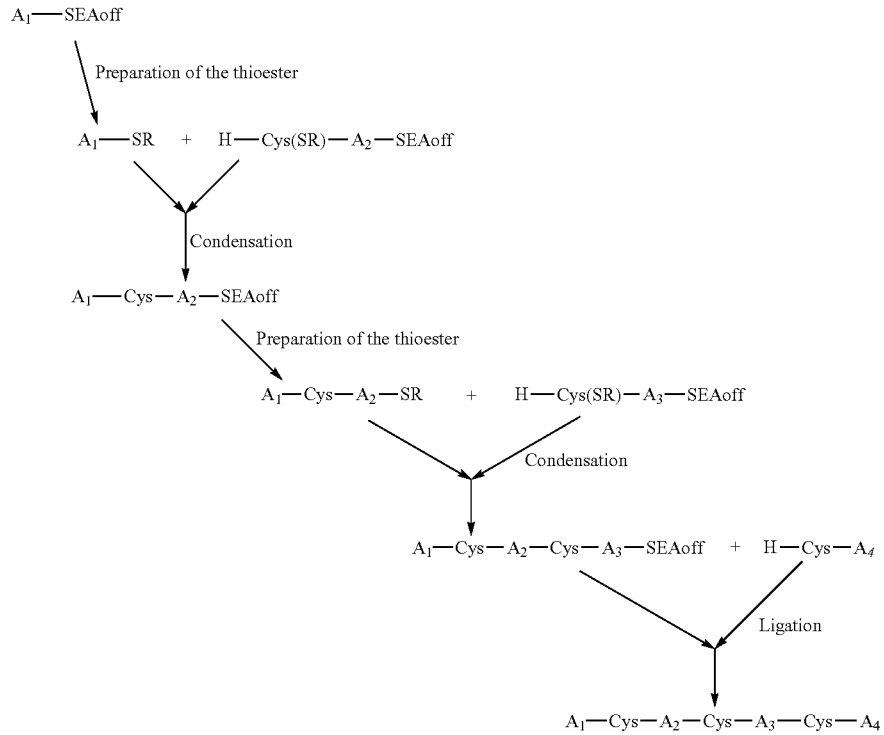

Diagram 2

The present invention also relates to the preparation of the peptide-thioesters of formula (II) from bis(2-sulphanylethyl) amino peptide: $A_1$-SEAoff according to the method described above, by the action of a thiol R—SH, in the presence of a cyclic disulphide reducing agent. The invention also relates to the peptide-thioesters thus obtained.

The polypeptides of formula (I) obtained according to the invention can be used to produce a polypeptide library, for example for screening purposes.

They can also be used for the manufacture of pharmaceutical compositions, in combination with one or more compatible and pharmaceutically acceptable adjuvants or vehicles. By way of examples of pharmaceutical compositions that can be obtained according to the invention, there can be mentioned medicaments that can be used for humans and for animals, and vaccine preparations.

They can also be used for producing diagnostic kits.

According to another subject of the present invention, the invention also relates to a method for manufacturing a pharmaceutical composition comprising:

the formulation or forming of this polypeptide in a form suitable for use for a diagnostic device.

The method according to the present invention is particularly useful as it makes it possible to synthesize, in total synthesis, a peptide chain formation of the desired length and nature, and comprising amino acid units with thiol substitution of the cysteine (Cys) or homocysteine type, distributed along the chain.

It has the advantage of being capable of being used on an industrial scale, due to the convergent synthesis which it involves, and this type of synthesis is particularly sought after with respect to the industrialization of methods since it provides advantageous yields, and in particular little loss in yield of products already developed, the synthesis cost of which is already high.

According to the present invention the SEA fragments allow the synthesis of proteins from the N-terminal end to the C-terminal end by successive ligation of peptide fragments.

Assembling from the N-terminal end to the C-terminal end offers a considerable advantage, compared with the reverse strategy of assembling from the C-terminal end to the N-terminal end, in fact, in this case the method induces self-purification of the peptide fragments which is very important in industrial synthesis.

According to another advantage the method of the invention makes it possible to use proteinogenic amino acids for the synthesis of the peptide fragments. It is therefore unnecessary to resort to the manufacture of amino acid derivatives (such as keto acids for example), which would make the synthesis considerably more difficult.

The following examples illustrate the present invention.

Example 1

One-Pot Assembly of 3 Fragments
1—Synthesis of the Peptide 1 (H-ILKEPVHGA-S(CH$_2$)$_2$COOH) (SEQ ID NO:2), Equivalent of A$_1$-SR with R=Alkyl, by Conversion of A$_1$-SEAoff in the Presence of an Alkylthiol R—SH, R=—(CH$_2$)$_2$COOH and a Cyclic Disulphide Reducing Agent.

The precursor peptide H-ILKEPVHGA-SEAoff (SEQ ID NO:2) was prepared as described by Ollivier N., Dheur J., Mhidia R., Blanpain A., and Melnyk O., Bis(2-sulphanyl-ethyl)amino native peptide ligation., Org. Lett. 12(22), 5238-41 (2010).

Tris(2-carboxyethyl)phosphine hydrochloride, TCEP,HCl (921.2 mg) is dissolved in 0.2 M phosphate buffer pH=7.3 (40 mL). 3-Mercaptopropionic acid (MPA) (2 mL) is added to this solution. The pH of the solution is readjusted to 4 with 5 N soda (approximately 3 mL).

The peptide H-ILKEPVHGA-SEAoff (SEQ ID NO:2) (40.31 mg) is dissolved in the preceding solution (40 mL). The reaction medium is placed under an inert atmosphere by means of 3 vacuum/argon cycles, and placed in a bath at 37° C.

After 22 hours, the reaction medium is transferred to a separating funnel. An aqueous solution containing 7% trifluoroacetic acid (TFA) (20 drops) is added. 4 extractions with diethyl ether are carried out. An aqueous solution containing 7% TFA (10 mL) is added and 3 new extractions with diethyl ether are carried out.

The aqueous phase is degassed for 13 minutes by bubbling argon through, before being purified in RP-HPLC (Nucleosil C18 column 120 A 5 pm, buffer A 100% water containing 0.05% TFA, buffer B CH3CN/water 4/1 containing 0.05% TFA, gradient: 0 to 10% of buffer B over 5 minutes then 10 to 100% of buffer B over 150 minutes, flow rate 6 mL/minute, 215 nm). 18.7 mg of pure peptide 1 (H-ILKEPVHGA-S(CH2)2COOH) (SEQ ID NO:15) is obtained (Yield=47.4%) C$_{47}$H$_{78}$N$_{12}$O$_{13}$S$_1$ MALDI-TOF [M+H]$^+$ calculated (monoisotopic mass) 1051.56; observed 1051.70.

2—Synthesis of Peptide 2 H—C(StBu)HHLEPGG-SEAoff (SEQ ID NO:3), Equivalent of H—C$_1$(SR)-A$_2$-SEAoff, with R=tBu Standard synthesis of a SEAoff peptide on a 0.25 mmol scale, according to:

Ollivier N., Dheur J., Mhidia R., Blanpain A., and Melnyk O., Bis(2-sulphanyl-ethyl)amino native peptide ligation., Org. Lett. 12(22), 5238-41 (2010).

The disulphide residue —S-t.Bu is coupled using Fmoc-Cys(St.Bu)-OH, in a manner analogous to the method described in Example 2 below.

The final deprotection and cleavage of the peptide from the resin are carried out with TFA/TIS/DMS/H20 (90/2.5/2.5/5/2.5 by volume, 25 mL) over 1 hour 30 minutes. The peptide is precipitated from a cold diethyl ether/heptane mixture (1/1 by volume), dissolved in a minimum amount of water and lyophilized. 132.6 mg of crude peptide are obtained (Yield=38%). C$_{43}$H$_{69}$N$_{13}$O$_{10}$S$_4$ MALDI-TOF [M+H]+ calculated (monoisotopic mass) 1056.42; observed 1056.10.

Part of peptide 2 is then oxidized before purification. For this, fragment 2 (122.6 mg) and I$_2$ (222.52 mg, 10 eq.) are dissolved in AcOH/water 4/1 (12.5 ml). After stirring for 10 minutes, the diluted reaction medium (total volume=37 mL) is transferred to a separating funnel containing diethyl ether (75 mL). 3 extractions with diethyl ether are carried out (3×75 mL). The aqueous phase is frozen and lyophilized in order to produce 94.3 mg of crude peptide.

After RP-HPLC purification (Nucleosil C18 column, 120 Å 5 μm, 215 nm, buffer A 100% water containing 0.05% TFA, buffer B CH3CN/water 4/1 containing 0.05% TFA, gradient: 0 to 10% of buffer B over 5 minutes, then 10 to 100% of buffer B over 150 minutes, flow rate 6 mL/minute) 40.52 mg of pure peptide is obtained (Yield=33%) C$_{43}$H$_{67}$N$_{13}$O$_{10}$S$_4$ MALDI-TOF [M+H]+ calculated 1054.4 (monoisotopic mass); observed 1054.4.

3) A$_1$-SR (Peptide 1) (R=CH$_2$CH$_2$CO$_2$H)+H—C$_1$(StBu)-A$_2$-SEAoff (Peptide 2)→A$_1$-C$_1$-A$_2$-SEAoff 4-mercaptophenylacetic acid (MPAA, 33.64 mg, 0.2 mmol, aromatic thiol) is dissolved in 0.1 M phosphate buffer pH=7.3 (1 mL). A 5 N soda solution (80 μL) is added to adjust the pH of the solution to 7.64. Peptide 1 (10.40 mg, 7.5 μmol) and peptide 2 (10.42 mg, 7.5 μmol) are dissolved together in the preceding solution (533 μL). The reaction medium is placed in a temperature-controlled bath at 37° C. under an inert atmosphere.

The ligation is monitored by RP-HPLC on an Xbridge BEH C18 column (4.6×250 mm, 300 Å, 5 μm) (215 nm, 1 mL/minute, 30° C., buffer A water containing 0.05% TFA, buffer B CH3CN/water 4/1 containing 0.05% TFA, 0-100% B over 30 minutes). For this, an aliquot (5 μL) of reaction medium is acidified with a solution of 10% TFA in water, extracted with diethyl ether to remove the MPAA and MPA before analysis.

4—Synthesis of Peptide 3 H—CILKEPVHGV-NH2 (SEQ ID NO:4), Equivalent of H—C$_2$-A$_3$ The preparation of the peptide H—C$_2$-A$_3$ is described in the publication by: Ollivier N., Dheur J., Mhidia R., Blanpain A., and Melnyk O., Bis(2-sulphanylethyl)amino native peptide ligation., Org. Lett. 12(22), 5238-41 (2010).

5—Protocol for One-Pot Ligation of Three Fragments.

Synthesis of Peptide 4 H-ILKEPVHGACHHLEPG-GCILKEPVHGV-NH2 (SEQ ID NO:5), Equivalent of A$_1$-C$_1$-A$_2$-C$_2$-A$_3$ Preparation of Peptide 4 from A$_1$-C$_1$-A$_2$-SEAoff and Peptide 3 (H—C$_2$-A$_3$)

A$_1$-C$_1$-A$_2$-SEAoff Converted to A$_1$-C$_1$-A$_2$-SEAon by Reduction in the Presence of TCEP (tris(2-carboxyethyl) phosphine)

After reacting for 5 hours 30 minutes, TCEP,HCl (tris(2-carboxyethyl)phosphine hydrochloride) (57.34 mg, 0.2 mmol) is dissolved in a 0.1 M phosphate buffer pH=7.3 (1 mL). A 5 N soda solution (140 μL) is added to adjust the pH of the solution to 7.33.

A$_1$-C$_1$-A$_2$-SEAon+(Peptide 3) H—C$_2$-A$_3$→A$_1$-C$_1$-A$_2$-C$_2$-A$_3$ (Peptide 4)

Peptide 3 (16.17 mg, 11.2 μmol) is dissolved in the preceding solution (533 μL) then added to the preceding reaction medium which is again placed under an inert atmosphere at 37° C.

The ligation is monitored by RP-HPLC on an Xbridge BEH CI8 column (4.6×250 mm, 300 A, 5 μm) (215 nm, 1 mL/minute, 30° C., buffer A water containing 0.05% TFA, buffer B CH3CN/water 4/1 containing 0.05% TFA, 0-100% B over 30 minutes). For this, an aliquot (5 μL) of reaction medium is acidified with a 10% TFA solution in water, extracted with diethyl ether to remove the MPAA (4-mercaptophenylacetic acid) before analysis.

When the reaction is complete, the reaction medium is diluted with water containing 0.05% TFA (3 mL) and a 10% TFA solution in water (15 drops) is added. After 5 extractions with diethyl ether (5×8 mL), the aqueous phase is degassed for 10 minutes by bubbling argon through. After purification by RP-HPLC on a Nucleosil C18 column 120 Å 5 μm (215 nm, flow rate 6 mL/minute, buffer A: water containing 0.05% TFA, buffer B: CH3CN/water 4/1 containing 0.05% TFA, gradient: 0-10% of buffer B over 5 minutes, then 10-100% of buffer B over 150 minutes) 16.2 mg of pure peptide 4 is obtained (59.2%).

Example 2

1—Synthesis of K1(Fragment 1)-MPA
a—Synthesis of K1(Fragment 1)-SEAoff (IIGKGRSYKGTVSITKSGI; SEQ ID NO:6)

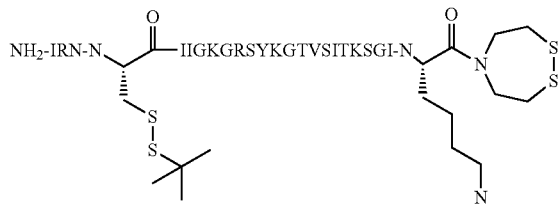

The SEA resin (0.5 mmol, 0.175 mmol/g) is conditioned in dichloromethane (DCM). Fmoc-Lys(Boc)-OH (2.342 g, 5 mmol) is dissolved in DCM and a few drops of dimethylformamide (DMF) in order to aid solubilization, then the solution is added to the resin. PyBrop (2.331 g, 5 mmol) is dissolved in a minimum amount of DCM then added to the resin. Diisopropylethylamine (DIEA) (2.613 mL, 15 mmol) is then added to the resin and cleavage takes 2 hours (total volume<5 mL). The resin is then washed for 3×2 minutes with DCM. The resin is then treated with 10% Ac₂O/5% DIEA/DCM (10 mL, 2 minutes) then (10 mL, 20 minutes). The resin is then washed for 5×2 minutes with DCM.

Fragment 1 is assembled on a portion of the preceding resin (0.25 mmol, 0.175 mmol/g) with a peptide synthesizer (CEM μWaves, Saclay, France) without using microwaves, using the Fmoc/tert-butyl strategy. The coupling is carried out with the amino acids (0.2 M, 4 eq), the activator HBTU (0.5 M, 3.6 eq.) and the base DIEA (2 M, 8 eq). The final deprotection and cleavage of the peptide from the resin are carried out with TFA/TIS/DMS/thioanisole/H₂O (90/2.5/2.5/2.5/2.5 by volume, 25 mL) for 2 hours 30 minutes. The peptide is precipitated from a cold diethyl ether/heptane mixture (1/1 by volume), dissolved in a minimum amount of water and lyophilized. 288 mg of crude peptide is obtained (Yield=32%). $C_{120}H_{216}N_{36}O_{31}S_4$ LC-MS [M+H]+ calculated (average mass) 2788.5; observed 2788.1.

A portion of fragment 1 is then oxidized before purification. For this, fragment 1 (95.7 mg) is dissolved in AcOH/water 1/4 (47.9 mL). 197 mM I₂ in DMSO (270 μL, 50 μmol, 2 eq.) is added to the preceding solution. After stirring for 30 seconds, 64.8 mM dithiothreitol (DTT, 823 μL, 50 μmol, 2 eq) is added to consume the remaining I₂ and injected directly into RP-HPLC.

After RP-HPLC purification (Nucleosil C18 column 120 Å, 5 μm, buffer A 100% water containing 0.05% TFA, buffer B CH₃CN/water 4/1 containing 0.05% TFA, gradient: 0 to 20% of buffer B in 5 minutes, then 20 to 40% in 40 minutes, flow rate 6 mL/minute, 215 nm) 25.8 mg of pure peptide is obtained (Yield=27%) $C_{120}H_{214}N_{36}O_{31}S_4$ MALDI-TOF [M+H]+ calculated (monoisotopic mass) 2784.52; observed 2784.6.

b—Synthesis of K1(Fragment 1)-MPA (IIGKGRSYKGTVSITKSGI; SEQ ID NO:6)

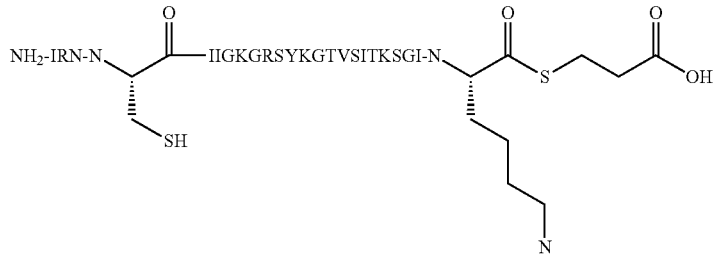

Tris(2-carboxyethyl)phosphine hydrochloride (TCEP, HCl, 229.63 mg, 0.8 mmol) is solubilized in 0.2 M sodium phosphate buffer pH=7.3 (10 mL). Mercaptopropionic acid (MPA, 0.5 mL) is added. NaOH 5M (340 μL) is added to adjust the pH to 3.98.

Fragment 1 K1-SEAoff (24.67 mg, 6.9 μmol) is dissolved in the preceding solution (10.3 mL). The reaction medium is heated to 37° C. under an argon atmosphere. The progress of the reaction is monitored by RP-HPLC on an Xbridge BEH C18 column (215 nm, 1 mL/minute, 30° C., eluent A water containing 0.05% trifluoracetic acid (TFA), eluent B CH₃CN/water 4/1 containing 0.05% TFA, 0-100% B in 30 minutes). For this, aliquots are acidified with an aqueous solution containing 10% TFA, extracted with Et₂O in order to remove the excess MPA before analysis.

After completion of the reaction, the reaction medium is diluted with water (10 mL) and an aqueous solution containing 10% TFA (5 mL) is added. After 3 extractions with Et₂O (3×15 mL) and bubbling argon through for 15 minutes, RP-HPLC purification takes place on a Nucleosil C18 column 120 Å, 5 μm (215 nm, 6 mL/minute, ambient temperature, eluent A water containing 0.05% TFA, eluent B CH3CN/water 4/1 containing 0.05% TFA, 0-10% B in 5 minutes, then 10-100% B in 150 minutes) provides 9.7 mg of pure K1(fragment 1)-MPA (41%).

2—Synthesis of StBu-K1(Fragment 2)-SEAoff (QP-WSSMIPHEHSFLPSSYRGKDLQEN; SEQ ID NO:7)

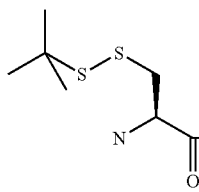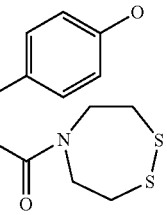

The resin SEA (0.5 mmol, 0.175 mmol/g) is conditioned in DCM. Fmoc-Tyr-OH (2.298 g, 5 mmol) is dissolved in DCM (<5 mL) and a few drops of DMF to aid solubilization, then added to the resin. PyBrop (2.331 g, 5 mmol) is dissolved in a minimum amount of DCM, then added to the resin. DIEA (2.614 mL, 15 mmol) is then added to the resin and the coupling takes 2 hours. The resin is then washed for 4×2 minutes with DCM. The resin is then treated with 10% Ac$_2$O/5% DiEA/DCM (10 mL, 2 minutes) then (10 mL, 20 minutes). The resin is then washed for 5×2 minutes with DCM.

Fragment 2 is assembled on the preceding resin (0.5 mmol, 0.175 mmol/g) with a peptide synthesizer (CEM μWaves, Saclay, France) without using microwaves, using the Fmoc/tert-butyl strategy. The coupling is carried out with the amino acids (0.2 M, 4 eq.), the activator HBTU (0.5 M, 3.6 eq.) and the base DIEA (2 M, 8 eq.). The washing solvent (DMF) as well as the Fmoc-Met-OH solvent contain 1% thioanisole for maximum prevention of the oxidation of the methionine of the sequence.

The resin is separated into 2 after the glutamine in position 2 (0.25 mmol) in order to couple the Fmoc-Cys (StBu)-OH manually. To do this, the resin is washed with DMF for 4×2 minutes, weighed in DMF and divided in 2. HBTU (379.3 mg, 1 mmol) is dissolved in DMF (1100 μL). HOBt (135 mg, 1 mmol) is dissolved in DMF (500 μL) and added to HBTU. Fmoc-Cys(StBu)-OH (431.6 mg, 1 mmol) is dissolved in DMF (500 μL) and added to the HBTU/HOBt mixture. DIEA (522.7 μL, 3 mmol) is then added to the mixture. After stirring for 1 minute the mixture is added to the resin and coupling takes 45 minutes. The resin is then washed with DMF for 4×2 minutes. Deprotection of the Fmoc N-terminal is carried out by treatment with 20% piperidine in DMF (15 minutes then 5 minutes). The resin is then washed for with DCM for 4×2 minutes then with Et$_2$O for 3×2 minutes and dried.

The final deprotection and cleavage of the peptide from the resin are carried out with TFA/TIS/DMS/Thioanisole/H$_2$O (90/2.5/2.5/2.5/2.5 by volume, 25 mL) for 2 hours 30 minutes. The peptide is precipitated from a cold diethyl ether/heptane mixture (1/1 by volume), dissolved in a minimum amount of water and lyophilized. 366.14 mg of crude peptide are obtained (yield=35.6%). $C_{156}H_{231}N_{41}O_{44}S_5$ MALDI-TOF [M+H]+ calculated (monoisotopic resolution) 3543.6; observed 3542.2.

A portion of fragment 2 is then oxidized before purification. For this, fragment 2 (67 mg) is dissolved in AcOH/water 1/4 (35 mL) then 144 mM I$_2$ in DMSO (223 μL) is added. After stirring for 30 seconds, 64.8 mM DTT in AcOH/water 1/4 (503 μL) is added to consume the excess I$_2$. After bleaching the solution, the medium is injected into RP-HPLC (Nucleosil C18 column, 120 A, 5 μm, 2×28 cm, 215 nm, buffer A 100% water containing 0.05% TFA, buffer B CH$_3$CN/water 4/1 containing 0.05% TFA, gradient: 0 to 10% of buffer B in 5 minutes, then 10 to 100% B in 150 minutes, flow rate 6 mL/minute) 11.5 mg of pure peptide is obtained (yield=17.2%) $C_{156}H_{229}N_{41}O_{44}S_5$ LC-MS [M+H]+ calculated (monoisotopic resolution) 3541.6; observed 3541.9.

3—Synthesis of K1(Fragment 3) (RNPRGEEGGPWCFTS-NPEVRYEVCDIPQCSE; SEQ ID NO:14)

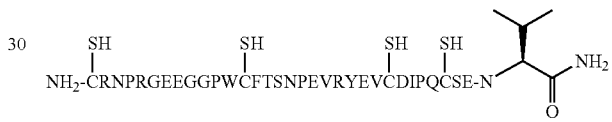

Fragment 3 is assembled on Novasyn TGR resin (0.5 mmol, 0.25 mmol/g) with a peptide synthesizer (CEM μWaves, Saclay, France) without using microwaves, using the Fmoc/tert-butyl strategy. The coupling is carried out with the amino acids (0.2 M, 4 eq.), the activator HBTU (0.5 M, 3.6 eq.) and the base DIEA (2 M, 8 eq.).

The final deprotection and cleavage of the peptide from the resin are carried out with TFA/EDT/H$_2$O/TIS (94/2.5/2.5/1 by volume, 30 mL) for 2 hours 30 minutes. The peptide is precipitated from a cold diethyl ether/heptane mixture (1/1 by volume), dissolved in a minimum amount of water and lyophilized. After RP-HPLC purification (Vydac C18 column 50 cm×2 cm, 280 nm, buffer A 100% water containing 0.05% TFA, buffer B CH$_3$CN/water 4/1 containing 0.05% TFA, gradient: 0 to 20% of buffer B in 10 minutes then 20 to 50% of buffer B in 60 minutes, flow rate 30 mL/minute) 272 mg of pure peptide is obtained (yield=13%) $C_{158}H_{239}N_{47}O_{52}S_4$ MALDI-TOF [M+H]+ calculated (monoisotopic resolution) 3755.6; observed 3755.7.

4—One-Pot Ligation Protocol:

Synthesis of Peptide 4 K1(125-209)

Guanidine HCl (573.24 mg, 6 mmol) is dissolved in 0.1 M phosphate buffer pH=7.3 (1 mL). 4-mercaptophenylacetic acid (MPAA, 33.68 mg, 0.2 mmol) is dissolved in the latter solution (1 mL). NaOH 5M (150 μL) is added to adjust the pH of the solution to 7.53.

K1(fragment 1)-MPA (9.71 mg, 2.8 μmol) and StBu-K1 (fragment 2)-SEA (10.65 mg, 2.6 μmol) are dissolved together in the preceding solution (185 μL). The reaction medium is placed in a temperature-controlled bath at 37° C. in a glove box.

Ligation is monitored by RP-HPLC on an Xbridge BEH C18 column (4.6×250 mm, 300 A, 5 μm) (215 nm, 1 mL/minute, 30° C., buffer A water containing 0.05% TFA, buffer B CH$_3$CN/water 4/1 containing 0.05% TFA, 0-100% B in 30 minutes). For this, an aliquot (1 µL) of reaction medium is acidified with an aqueous solution containing 10% TFA, extracted with Et$_2$O to remove the MPAA and MPA before analysis.

After reacting for 20 hours, guanidine HCl (573.15 mg, 6 mmol) is dissolved in 0.1 M phosphate buffer, pH=7.3 (1 mL). Tris(2-carboxyethyl) phosphine hydrochloride (TCEP, HCl, 57.59 mg, 0.2 mmol) is dissolved in the latter solution (1 mL). 5M NaOH is added to adjust the pH of the solution to 7.27.

K1(fragment 3) (16.46 mg, 3.9 µmol) is dissolved in the preceding solution (185 µL) then added to the preceding reaction medium which is again placed under an inert atmosphere at 37° C.

The reaction medium (7.6 mL) is then transferred in several goes into a 2 mL Vivaspin ultrafiltration system with an MWCO of 3000 and ultrafiltered at 12000 rcf, at 12° C. for 3 hours 20 minutes. Once concentrated, the reaction medium is approximately 800 µL.

It is then dialyzed at 4° C. in a dialysis cassette with an MWCO cut-off of 3500 with a 10 mM PBS buffer, 138 mM NaCl, 2.7 mM KCl pH=7.4 containing 10% by volume of glycerol (1 L) overnight. The reaction medium is approximately 1 mL after dialysis.

Folded K1 (125-209) is assayed at 562 nm using the BCA Protein Assay kit (Pierce) producing a BSA standard range. The estimated concentration of K1 (125-209) is 137 µM.

Example 3

1—Synthesis of K1 (Fragment 3)-Biotin (CRNPRGEEGG-PWCFTSNPEVRYEVCDIPQCSEV; SEQ ID NO:9)

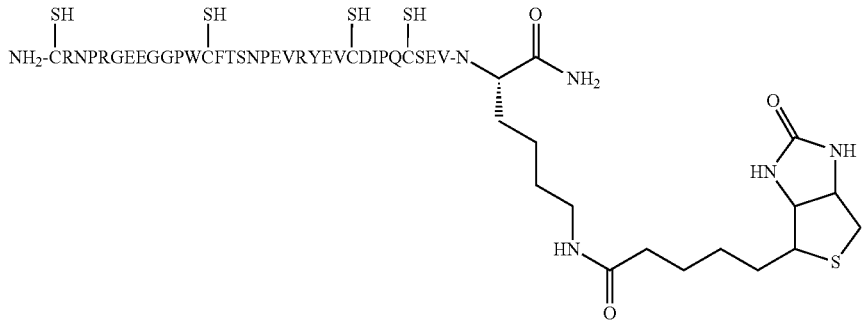

The ligation is monitored by RP-HPLC on an Xbridge BEH C18 column (4.6×250 mm, 300 A, 5 µm) (215 nm, 1 mL/minute, 30° C., buffer A water containing 0.05% TFA, buffer B CH$_3$CN/water 4/1 containing 0.05% TFA, 0-100% B in 60 minutes). For this, an aliquot (1 µL) of reaction medium is acidified with an aqueous solution containing 10% TFA, extracted with Et$_2$O to remove the MPAA and MPA before analysis.

$C_{418}H_{648}N_{122}O_{127}S_7$ MALDI-TOF [M+H]$^+$ (average mass) calculated 9640.01, found 9639.

When the reaction is complete, the reaction medium is diluted with water (4 mL) and an aqueous solution containing 10% TFA (1 mL) is added. After 4 extractions with Et$_2$O (4×8 mL), the aqueous phase is degassed for 10 minutes by bubbling argon through, diluted with water (36 mL) and filtered. The frit is rinsed with AcOH (1 mL) and rinsed with water (20 mL). The mixture is purified by RP-HPLC on a Vydac C18 column 300 Å, 5 µm (215 nm, 20 mL/minute, buffer A water containing 0.05% TFA, buffer B CH3CN/water 4/1 containing 0.05% TFA, 0-20% B in 5 minutes, then 20-60% B in 80 minutes) 11.46 mg of pure K1 (125-209) is obtained (Yield=39.4%).

5—Folding of K1(125-209)

K1(125-209) (3.99 mg, 0.355 µmol) is dissolved in 10 mM PBS buffer, 138 mM NaCl, 2.7 mM KCl pH=7.4 containing 10% by volume of glycerol, 1 mM reduced glutathion, 0.2 mM oxidized glutathion (10 mL).

The reaction medium is placed at 4° C.

The folding is monitored by LC-MS on an Xbridge BEH C18 column (4.6×250 mm, 300 A, 5 µm) (215 nm, 1 mL/minute, 30° C., buffer A water containing 0.1% TFA, buffer B CH$_3$CN/water 4/1 containing 0.1% TFA, 0-100% B in 60 minutes).

After 65 hours, the reaction medium is ultracentrifuged at 8000 rcf, at 4° C. for 15 minutes then at 9000 rcf, at 4° C. for 15 minutes in order to remove some aggregates.

Fmoc-Lys(Biotin)-OH (2×89 mg, 2×0.15 mmol) is coupled twice on PAL-ChemMatrix resin (0.1 mmol, 0.43 mmol/g) using TBTU (2×30.5 mg, 2×0.15 mmol) and DIEA (2×50 µL, 2×0.45 mmol) for 2 hours in NMP. After washings with NMP (3×2 minutes) and DMF (3×2 minutes), the 3-biotin fragment is assembled on two 50 µmol columns with a peptide synthesizer (INTAVIS) using the Fmoc/tert-butyl strategy.

The couplings are carried out using 4 eq. of each amino acid, 3.6 eq. HBTU, and 8 eq. DIEA. A stage of capping is carried out after each coupling with Ac$_2$O/DIEA. On completion of the synthesis, the resin is washed with CH$_2$Cl$_2$, diethyl ether (2×2 minutes) and dried under vacuum.

The final deprotection and cleavage of the peptide from the resin are carried out with TFA/EDT/H$_2$O/TIS (94/2.5/2.5/1 by volume, 2×5 mL) for 2 hours. The peptide is precipitated from a cold diethyl ether/heptane mixture (1/1 by volume), dissolved in a minimum amount of water and lyophilized. After RP-HPLC purification (Nucleosil C18 column 50 cm×2 cm, 215 nm, buffer A 100% water containing 0.05% TFA, buffer B CH$_3$CN/water 4/1 containing 0.05% TFA, gradient: 0 to 15% of buffer B in 5 minutes then 15 to 35% of buffer B in 60 minutes, flow rate 6 mL/minute) 36.75 mg of pure peptide is obtained (yield=8%)

$C_{174}H_{265}N_{51}O_{55}S_5$ MALDI-TOF [M+H]+ calculated (average mass) 4112.68; observed 4114.3.

2—One-Pot Ligation Protocol:

Synthesis of a 4 K1(125-209) K-Biotin Peptide

Guanidine HCl (573.28 mg, 6 mmol) is dissolved in 0.1 M phosphate buffer pH=7.3 (1 mL). 4-mercaptophenylacetic acid (MPAA, 33.59 mg, 0.2 mmol) is dissolved in the latter solution (1 mL). NaOH 5M (80 µL) is added to adjust the pH of the solution to 7.40.

The K1(fragment 1)-MPA (2.76 mg, 0.8 μmol) and the StBu-K1(fragment 2)-SEA (3.30 mg, 0.8 μmol) are dissolved together in the preceding solution (57 μL). The reaction medium is placed in a temperature-controlled bath at 37° C. in a glove box.

The ligation is monitored by RP-HPLC on an Xbridge BEH C18 column (4.6×250 mm, 300 Å, 5 μm) (215 nm, 1 mL/minute, 30° C., buffer A water containing 0.05% TFA, buffer B CH$_3$CN/water 4/1 containing 0.05% TFA, 0-100% B in 30 minutes). For this, an aliquot (1 μL) of reaction medium is acidified with an aqueous solution containing 10% TFA, extracted with Et$_2$O to remove MPAA and MPA before analysis.

After reacting for 24 hours 40 minutes, guanidine, HCl (573.18 mg, 6 mmol) is dissolved in 0.1 M phosphate buffer, pH=7.3 (1 mL). Tris(2-carboxyethyl)phosphine hydrochloride (TCEP,HCl, 57.80 mg, 0.2 mmol) is dissolved in the latter solution (1 mL). 5M NaOH is added to adjust the pH of the solution to 7.40.

The K1(fragment 3) (5.50 mg, 1.2 μmol) is dissolved in the preceding solution (57 μL) then added to the preceding reaction medium which is again placed under an inert atmosphere at 37° C.

The ligation is monitored by RP-HPLC on an Xbridge BEH C18 column (4.6×250 mm, 300 Å, 5 μm) (215 nm, 1 mL/minute, 30° C., buffer A water containing 0.05% TFA, buffer B CH$_3$CN/water 4/1 containing 0.05% TFA, 0-100% B in 60 minutes). For this, an aliquot (1 μL) of reaction medium is acidified with an aqueous solution containing 10% TFA, extracted with Et$_2$O to remove MPAA and MPA before analysis.

$C_{434}H_{674}N_{126}O_{130}S_8$ [M+H]$^+$ expected (average mass) 9994.49, observed 9994.41.

On completion of the reaction, the reaction medium was diluted with water and an aqueous solution containing 10% TFA. After extractions with Et$_2$O, the aqueous phase was degassed by bubbling argon through, diluted with water, filtered and purified by RP-HPLC on a Vydac C18 column 300 Å, 5 μm (215 nm, 20 mL/minute, buffer A water containing 0.05% TFA, buffer B CH3CN/water 4/1 containing 0.05% TFA).

Fragment 1 and fragment 2: K1(fragment 1)-MPA and StBu-K1(fragment 2)-SEA are prepared as described previously in Example 2.

Examples of Preparation of the Starting Peptide Fragments

A) The synthesis of the SEAon peptide fragments is carried out according to Ollivier N., Dheur J., Mhidia R., Blanpain A., and Melnyk O., Bis(2-sulphanylethyl)amino native peptide ligation., Org. Lett. 12(22), 5238-41 (2010).

By way of illustration the preparation of the peptide fragments

```
(1a):H-ILKEPVHGG-N(CH2CH2SH)2,       (SEQ ID NO: 10)

(1b):H-ILKEPVHGA-N(CH2CH2SH)2,       (SEQ ID NO: 15)

(1c):H-ILKEPVHGV-N(CH2CH2SH)2       (SEQ ID NO: 11)
and (1d):H-ILKEPVHGY-N(CH2CH2SH)2       (SEQ ID NO: 12)
``` is carried out in solid phase

Peptide fragment (1a) is obtained from the primer support prepared with glycine.

Peptide fragment (1b) is obtained from the primer support prepared with alanine.

Peptide fragment (1c) is obtained from the primer support prepared with valine.

Peptide fragment (1d) is obtained from the primer support prepared with tyrosine.

The synthesis of the polypeptides can be summarized as follows:

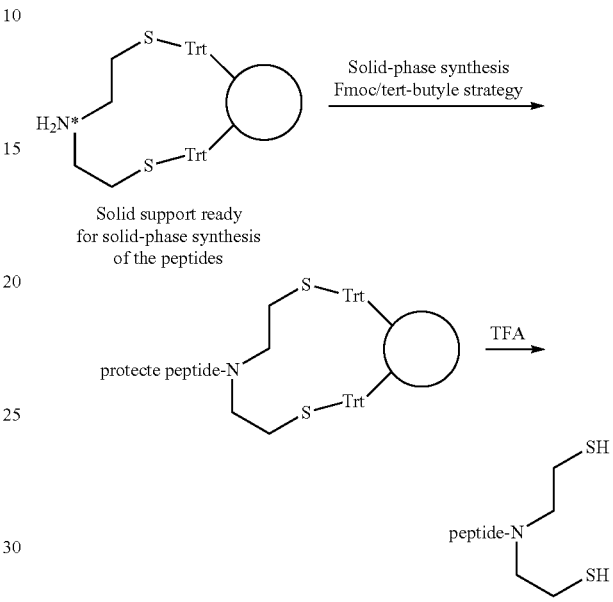

The peptide fragments thus obtained have the following general formula (ILKEPVHG; SEQ ID NO:13):

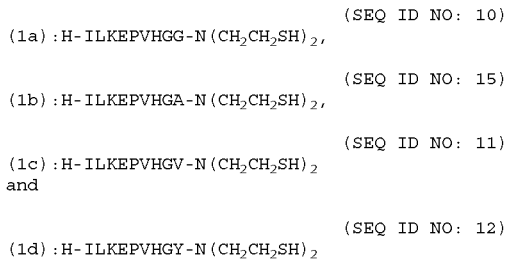

R = H 1c
R = CH$_3$ 1d
R = CH(CH$_2$)$_2$ 1e
R = p-OHPhCH$_2$ 1f

Solid phase synthesis of the different polypeptides is carried out using the Fmoc/tert-butyl strategy on resins (scale of 0.1 mmol) on a microwave peptide synthesizer (CEM μWAVES, Saclay, France). The coupling is carried out in using a 5-times molar excess of each amino acid, the activator HBTU is used with a 4.5-times molar excess and the base DiEA is used with a 10-times molar excess.

The final deprotection and cleavage of the polypeptide from the resin are carried out with 10 mL of a TFA/TIS/DMS/H$_2$O mixture (92.5/2.5/2.5/2.5 by volume) for 1 hour. The polypeptide is then obtained by precipitation from 100 mL of a diethyl ether/heptane mixture (1/1 by volume), dissolved in H$_2$O then lyophilized.

The purity of each peptide fragment is determined by HPLC (91% for peptide fragment (1a) with a glycine, 83% for peptide fragment (1b), 80% for (1c), and 88% for (1d)). MALDI-Tof analysis of the peptide fragments is consistent with the structure of the expected peptide fragment (Peptide fragment (1a) $C_{47}H_{81}N_{13}O_{11}S_2$ [M+H]+ calculated 1068.6 Da, observed 1068.5. Peptide fragment (1b) $C_{48}H_{83}N_{13}O_{11}S_2$ [M+H]+ calculated 1082.6 Da, observed 1082.4. Peptide fragment (1c) $C_{50}H_{87}N_{13}O_{11}S_2$ [M+H]+ calculated 1110.6 Da, observed 1110.5). Peptide fragment 1(d) $C_{54}H_{87}N_{13}O_{12}S_2$ [M+H]+ calculated 1174.6 Da, observed 1174.6).

Purification of the polypeptides is carried out on a Nucleosil C18 column in acetonitrile-$H_2O$ (80-20) in TFA, with a gradient of 0 to 30% in 30 minutes for peptide fragment (1a), and a gradient of 0 to 10% in 5 minutes then 10 to 25% in 25 minutes for peptide fragments (1b) and (1c).

The purity determined by HPLC is 96% for peptide fragment (1a) with an overall yield of 35%, 97% for peptide fragment (1b) with a yield of 31%, and of 99% for peptide fragment (1c) with a yield of 27%.

B) Oxidation of Peptide Fragments (1a), (1b), (1c) and (1d) to Dithiazepanes

Peptide fragments (1a), (1b), (1c) and (1d) as obtained previously are oxidized according to the following diagram general:

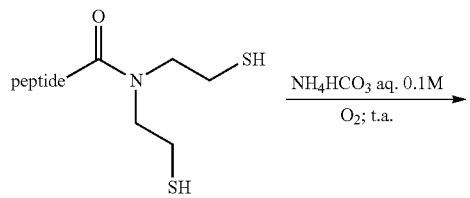

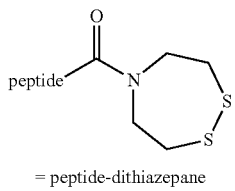

= peptide-dithiazepane

Each peptide fragment is cleaved from the solid support by the action of a TFA/DMS/TiS/$H_2O$ solution (92.5/2.5/2.5/2.5; v/v). The peptide fragment is then precipitated from a large volume of a diethyl ether/heptane mixture (1/1; v/v) and washed twice using this solution. The crude peptide fragment lyophilized after the cleavage stage is then dissolved in a 0.1M ammonium bicarbonate solution previously degassed for 10 minutes by bubbling nitrogen through (1 mg/mL).

The mixture is then left at ambient temperature under vigorous stirring. The development of the reaction is followed by MALDI-TOF mass spectrometry until the complete disappearance of the reduced form of the polypeptide considered. The polypeptide is finally purified by RP-HPLC (gradient eluent A ($H_2O$/0.05% TFA)/eluent B (80% Acetonitrile/20% $H_2O$/0.05% TFA): 0 to 10% in 10 minutes then 10% to 25% in 25 minutes) then frozen and lyophilized.

The table below summarizes the results obtained (MALDI-TOF analysis).

| peptide fragment | m/z $[M + H]^+_{calc.}$ | M/z $[M + H]^+_{obs.}$ | Final yield(%) |
|---|---|---|---|
| (1a) | 1066.6 | 1066.6 | 17 |
| (1b) | 1080.6 | 1080.6 | 13 |
| (1c) | 1108.6 | 1108.6 | 23 |
| (1d) | 1172.6 | 1172.6 | 20 |

The invention claimed is:

1. A method for preparing a peptide assembly of n fragments and n−1 amino acids bearing a thiol moiety, represented by the formula:

$$A_1\text{-}C_1\text{-}A_2\text{-}C_2\text{-}A_3\text{-} \ldots \text{-}C_{i-1}\text{-}A_i\text{-} \ldots \text{-}C_{n-1}\text{-}A_n \qquad (I)$$

in which $A_1, A_2, A_3, \ldots A_i \ldots, A_n$ are peptide fragments, $C_1, C_2, C_3 \ldots C_{i-1} \ldots C_{n-1}$ are amino acid residues bearing a thiol moiety, n is comprised between 3 and 50, and i is any integer comprised between 2 and n, the method comprising the steps of treating a bis(2-sulphanylethyl)amino peptide: $A_1$-SEAoff in which SEAoff is a cyclic bis(2-sulphanylethyl)amino group

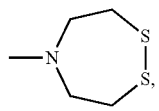

with a thiol R—SH, in the presence of a cyclic disulphide reducing agent to prepare a peptide-thioester of formula:

$$A_1\text{-SR} \qquad (II)$$

in which $A_1$ is a peptide fragment and SR is an alkyl thioester residue, R being able to be an optionally substituted alkyl radical, preparing a peptide fragment of formula (IV) by condensing a peptide fragment of structure:

$$H\text{—}C_1(SR')\text{-}A_2\text{-SEAoff} \qquad (III)$$

in which $C_1$, $A_2$ and SEAoff are defined as above and (SR') represents a disulphide residue on the thiol of the amino acid $C_1$, with the peptide thioester of formula (II) in the presence of an aromatic thiol ArSH, to obtain the peptide fragment of structure:

$$A_1\text{-}C_1\text{-}A_2\text{-SEAoff} \quad (IV)$$

in which $A_1$, $C_1$, $A_2$ and SEAoff are as defined previously, preparing a peptide thioester of formula:

$$A_1\text{-}C_1\text{-}A_2\text{-SR} \quad (II')$$

in which $A_1$, $C_1$, $A_2$ and R are as defined previously, by treating the peptide fragment of formula (IV) with a thiol R—SH, in the presence of a cyclic disulphide reducing agent, preparing a peptide fragment of formula (IV') by condensing a peptide fragment of structure:

$$H\text{—}C_2(SR')\text{-}A_3\text{-SEAoff} \quad (III')$$

in which SEAoff and R' and $C_2$ and $A_3$ are defined as above, with the peptide thioester of formula (II') in the presence of an aromatic thiol (ArSH), in order to produce a peptide fragment of structure:

$$A_1\text{-}C_1\text{-}A_2\text{-}C_2\text{-}A_3\text{-SEAoff} \quad (IV')$$

in which $A_1$, $C_1$, $A_2$, $C_2$, $A_3$ and SEAoff are as defined previously, and reiterating these 2 operations up to n−2 times, in order to obtain a peptide fragment of structure:

$$A_1\text{-}C_1\text{-}A_2\text{-}C_2\text{-}A_3\text{-} \ldots \text{-}C_{i-1}\text{-}A_i\text{-} \ldots \text{-}C_{n-2}\text{-}A_{n-1}\text{-SEAoff} \quad (IV''')$$

in which $A_1$, $A_2$, $A_3$, ... $A_i$ ..., $A_{n-1}$, $C_1$, $C_2$, $C_3$ ... $C_{i-1}$ ... $C_{n-2}$ and SEAoff are as defined previously, followed by implementing a native ligation reaction of this obtained peptide fragment (IV'''), with a peptide of formula:

$$H\text{—}C_{n-1}\text{-}A_n (V'')$$

in which $C_{n-1}$ and $A_n$ are as defined previously, in the presence of a cyclic disulphide reducing agent, in order to produce the multiple peptide assembly of general formula (I) wherein assembly proceeds from the peptide N-terminal end to the C-terminal end, and wherein a peptide assembly of n fragments is prepared in a "one pot" reaction in the absence of a step of isolating intermediates.

2. A method according to claim 1, wherein a peptide assembly of 3 or 4 fragments is prepared, of structures $A_1\text{-}C_1\text{-}A_2\text{-}C_2\text{-}A_3$ or $A_1\text{-}C_1\text{-}A_2\text{-}C_2\text{-}A_3\text{-}C_3\text{-}A_4$.

3. A method according to claim 1, wherein $C_1$, $C_2$, $C_3$ ... $C_{i-1}$ ... $C_{n-1}$ represent Cys residues.

4. A method according to claim 1, wherein one or more of the peptide fragments $A_2$ ... $A_i$ ... $A_{n-1}$ can bear one or more modified amino acids.

5. A method according to claim 1, wherein the condensing of the peptide-thioester with a peptide fragment of structure (III) is carried out in the presence of 4-mercaptophenylacetic acid.

6. A method for manufacturing a pharmaceutical composition wherein the method comprises:
manufacturing a polypeptide of formula (I) according to claim 1, and
preparing a pharmaceutical composition comprising a polypeptide or peptide thus prepared, in the pure state or in combination with one or more compatible and pharmaceutically acceptable adjuvants.

7. A method for manufacturing a diagnostic device wherein the method comprises:
manufacturing a polypeptide of formula (I) according to claim 1, and
preparing a formulation or forming of this polypeptide in a form suitable for use for a diagnostic device.

8. A method according to claim 1, wherein the cyclic disulphide reducing agent is tris(2-carboxyethyl)phosphine.

9. A method according to claim 1, wherein n is comprised between 3 and 20.

10. A method according to claim 1, wherein n is comprised between 3 and 10.

* * * * *

SEQUENCE LISTING

```
<160> NUMBER OF SEQ ID NOS: 15

<210> SEQ ID NO 1
<211> LENGTH: 8
<212> TYPE: PRT
<213> ORGANISM: artificial sequences
<220> FEATURE:
<221> NAME/KEY: SOURCE
<222> LOCATION: 1..8
<223> OTHER INFORMATION: /sequence is synthetized

<400> SEQUENCE: 1

Gly Phe Gly Gln Gly Phe Gly Gly
1               5

<210> SEQ ID NO 2
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /sequence is synthetized

<400> SEQUENCE: 2

Ile Leu Lys Glu Pro Val His Gly Ala
```

```
1               5

<210> SEQ ID NO 3
<211> LENGTH: 7
<212> TYPE: PRT
<213> ORGANISM: artificial sequences
<220> FEATURE:
<221> NAME/KEY: SOURCE
<222> LOCATION: 1..7
<223> OTHER INFORMATION: /sequence is synthetized

<400> SEQUENCE: 3

His His Leu Glu Pro Gly Gly
1               5

<210> SEQ ID NO 4
<211> LENGTH: 10
<212> TYPE: PRT
<213> ORGANISM: artificial sequences
<220> FEATURE:
<221> NAME/KEY: SOURCE
<222> LOCATION: 1..10
<223> OTHER INFORMATION: /sequence is synthetized

<400> SEQUENCE: 4

Cys Ile Leu Lys Glu Pro Val His Gly Val
1               5                   10

<210> SEQ ID NO 5
<211> LENGTH: 27
<212> TYPE: PRT
<213> ORGANISM: artificial sequences
<220> FEATURE:
<221> NAME/KEY: SOURCE
<222> LOCATION: 1..27
<223> OTHER INFORMATION: /sequence is synthetized

<400> SEQUENCE: 5

Ile Leu Lys Glu Pro Val His Gly Ala Cys His His Leu Glu Pro Gly
1               5                   10                  15

Gly Cys Ile Leu Lys Glu Pro Val His Gly Val
            20                  25

<210> SEQ ID NO 6
<211> LENGTH: 19
<212> TYPE: PRT
<213> ORGANISM: artificial sequences
<220> FEATURE:
<221> NAME/KEY: SOURCE
<222> LOCATION: 1..19
<223> OTHER INFORMATION: /sequence is synthetized

<400> SEQUENCE: 6

Ile Ile Gly Lys Gly Arg Ser Tyr Lys Gly Thr Val Ser Ile Thr Lys
1               5                   10                  15

Ser Gly Ile

<210> SEQ ID NO 7
<211> LENGTH: 26
<212> TYPE: PRT
<213> ORGANISM: artificial sequences
<220> FEATURE:
<221> NAME/KEY: SOURCE
<222> LOCATION: 1..26
<223> OTHER INFORMATION: /sequence is synthetized

<400> SEQUENCE: 7
```

Gln Pro Trp Ser Ser Met Ile Pro His Glu His Ser Phe Leu Pro Ser
1               5                   10                  15

Ser Tyr Arg Gly Lys Asp Leu Gln Glu Asn
            20                  25

<210> SEQ ID NO 8
<211> LENGTH: 32
<212> TYPE: PRT
<213> ORGANISM: artificial sequences
<220> FEATURE:
<221> NAME/KEY: SOURCE
<222> LOCATION: 1..32
<223> OTHER INFORMATION: /sequence is synthetized

<400> SEQUENCE: 8

Cys Arg Asn Pro Arg Gly Glu Glu Gly Pro Trp Cys Phe Thr Ser
1               5                   10                  15

Asn Pro Glu Val Arg Tyr Glu Val Cys Asp Ile Pro Gln Cys Ser Glu
            20                  25                  30

<210> SEQ ID NO 9
<211> LENGTH: 33
<212> TYPE: PRT
<213> ORGANISM: artificial sequences
<220> FEATURE:
<221> NAME/KEY: SOURCE
<222> LOCATION: 1..33
<223> OTHER INFORMATION: /sequence is synthetized

<400> SEQUENCE: 9

Cys Arg Asn Pro Arg Gly Glu Glu Gly Pro Trp Cys Phe Thr Ser
1               5                   10                  15

Asn Pro Glu Val Arg Tyr Glu Val Cys Asp Ile Pro Gln Cys Ser Glu
            20                  25                  30

Val

<210> SEQ ID NO 10
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /sequence is synthetized

<400> SEQUENCE: 10

Ile Leu Lys Glu Pro Val His Gly Gly
1               5

<210> SEQ ID NO 11
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /sequence is synthetized

<400> SEQUENCE: 11

Ile Leu Lys Glu Pro Val His Gly Val
1               5

<210> SEQ ID NO 12
<211> LENGTH: 9
<212> TYPE: PRT
<213> ORGANISM: artificial sequences

```
<220> FEATURE:
<221> NAME/KEY: SOURCE
<222> LOCATION: 1..9
<223> OTHER INFORMATION: /sequence is synthetized

<400> SEQUENCE: 12

Ile Leu Lys Glu Pro Val His Gly Tyr
1               5

<210> SEQ ID NO 13
<211> LENGTH: 8
<212> TYPE: PRT
<213> ORGANISM: artificial sequences
<220> FEATURE:
<221> NAME/KEY: SOURCE
<222> LOCATION: 1..8
<223> OTHER INFORMATION: /sequence is synthetized

<400> SEQUENCE: 13

Ile Leu Lys Glu Pro Val His Gly
1               5

<210> SEQ ID NO 14
<211> LENGTH: 31
<212> TYPE: PRT
<213> ORGANISM: artificial sequences
<220> FEATURE:
<221> NAME/KEY: SOURCE
<222> LOCATION: 1..31
<223> OTHER INFORMATION: /sequence is synthetized

<400> SEQUENCE: 14

Arg Asn Pro Arg Gly Glu Glu Gly Gly Pro Trp Cys Phe Thr Ser Asn
1               5                   10                  15

Pro Glu Val Arg Tyr Glu Val Cys Asp Ile Pro Gln Cys Ser Glu
            20                  25                  30

<210> SEQ ID NO 15
<211> LENGTH: 9
<212> TYPE: PRT
<213> ORGANISM: artificial sequences
<220> FEATURE:
<221> NAME/KEY: SOURCE
<222> LOCATION: 1..9
<223> OTHER INFORMATION: /sequence is synthetized

<400> SEQUENCE: 15

Ile Leu Lys Glu Pro Val His Gly Ala
1               5
```